United States Patent
To

(10) Patent No.: US 9,468,651 B1
(45) Date of Patent: Oct. 18, 2016

(54) METHOD OF REMOVING MOLES

(76) Inventor: Yuk Ming To, Kowloon (HK)

(*) Notice: Subject to any disclaimer, the term of this patent is extended or adjusted under 35 U.S.C. 154(b) by 1527 days.

(21) Appl. No.: 12/650,232

(22) Filed: Dec. 30, 2009

(51) Int. Cl.
*A61K 33/12* (2006.01)
*A01N 59/06* (2006.01)
*A61K 33/00* (2006.01)

(52) U.S. Cl.
CPC ..................................... *A61K 33/00* (2013.01)

(58) Field of Classification Search
None
See application file for complete search history.

(56) References Cited

U.S. PATENT DOCUMENTS 2,373,933 A * 4/1945 Weeks .......................... 424/401

OTHER PUBLICATIONS

Schwartz, Robert A.; Skin Cancer: Recognition and Management; Blackwell Publishing; 2008, p. 350-366.*
Rodeheaver, G. T.; Hiebert, J. M.; Edlich, R. F. Comprehensive Therapy; 1982, vol. 8, issue 5, p. 37-43.*
Potassium Hydroxide MSDS sheet http://www.sciencelab.com/msds.php?msdsId=9927230.*
Ergoutou http://www.topbeijingtravel.com/beijing-food-restaurant/beijing-erguotou.htm.*

* cited by examiner

*Primary Examiner* — Mina Haghighatian
*Assistant Examiner* — Erin Hirt
(74) *Attorney, Agent, or Firm* — Egbert Law Offices, PLLC

(57) ABSTRACT

A method for removing moles includes applying a composition containing potassium hydroxide, Beijing Er Guo Tou and talcum powder on the surface of moles on human skin. The composition is applicable to benign moles and not to cancerous moles.

1 Claim, No Drawings

METHOD OF REMOVING MOLES

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to the field of mole removal. More particularly, the present invention relates to a method and composition for the removal of benign moles.

2. Description of Related Art Including Information Disclosed Under 37 CFR 1.97 and 37 CFR 1.98

Benign moles (hereinafter referred to as "nevus") are lesions of the skin. See Mellonis Illustrated Medical Dictionary 3rd Ed, New York Parthenon Publication Group, 1993. They are normally brown or black in colour. Nevus may be flat or protruding.

Nevus are normally round or oval in shape, but can have different shapes. Sizes ranges from 1 to 2 millimeters to several centimeters in diameter. The emergence of nevus does not cause discomfort or pain to the patient.

One or more nevi may be present at birth. Genetic factors and exposure to sunlight may be relevant to the numbers of nevi on the skin.

Nevus removal is usually done by surgery or laser surgery. Patients may feel pain in the removal process. Scarring may result after the surgery.

BRIEF SUMMARY OF THE INVENTION

This invention is to use a simple and effective method to removing nevus painlessly. By applying the mixture on the nevus by the following steps, the nevus will be removed in about 1 to 2 weeks. No scars will be left on the skin.

DETAILED DESCRIPTION OF THE INVENTION

First, sterilize and clean the patient's nevus with alcohol by a cotton bud. About 1 minute later, pick up an appropriate quantity of the mixture by a toothpick. Apply the mixture on the surface of the nevus. Let the mixture stay on the nevus for about 10 minutes.

After the time aforesaid, use a cotton bud to remove the mixture. Depending on the age of the patient and the size of the nevus, after a period of 7 to 14 days, a scab will be formed on the patient's nevus.

After the formation of the scab, the nevus will fall off by itself. After the falling of the nevus, the skin will become smooth and scarless.

Potassium hydroxide is an inorganic compound, it is usually produced by electrolysis. See The Merck Index, 12th Ed., Merck & Co. Whitehouse Station, N.J. 1996. It is white or slightly yellow, in lumps or in rods shape. Potassium hydroxide is strongly alkalic. It has a PH value of 13.5. It can be uses as an ingredient in soap or disinfectant.

Beijing Er Guo To is a colourless strong spirit produced in the northern part of China. See White wine blending techniques questions and answers: Li Tai He, Beijing Light Industry. It has 56% alcohol content. It is one of the favorite wines in the northern part of China. It is produced by using sorgham as the main ingredient for fermentation; followed by two times of distillation.

Talcum powder is a white or light greyish powder of natural mineral crystals. See Concise Encyclopedia of Chemical Technology 14th Ed., Wiley 1999. It is alkalic (a pH value of 9.0). It is often used as baby powder.

I claim:

1. A method of removing a mole from a human body, the method comprising:
    mixing a proportion corresponding to 100 milligrams of potassium hydroxide and one milliliters of Beijing er gou Tou and 500 milligrams of talcum powder so as to form an applicable mixture having a pH of 13.3;
    applying the applicable mixture to the mole for a period of ten minutes;
    removing the applied applicable mixture from the mole; and
    removing the mole after seven days.

* * * * *